United States Patent [19]

Jackson

[11] 4,020,849

[45] May 3, 1977

[54] CUFF INFLATION FOR TRACHEAL TUBES

[76] Inventor: Richard R. Jackson, Eight Trinity Road, Marblehead, Mass. 01947

[22] Filed: Dec. 1, 1975

[21] Appl. No.: 636,691

[52] U.S. Cl. .............................. 128/351; 128/274; 137/859

[51] Int. Cl.² ............................. A61M 25/00

[58] Field of Search ......... 128/145.6, 146.4, 146.5, 128/274, 349 B, 349 BV, 351; 137/522, 525, 859; 251/61.1

[56] References Cited

UNITED STATES PATENTS

| | | | |
|---|---|---|---|
| 2,715,418 | 8/1955 | Van Derbeck | 251/61.1 X |
| 2,908,286 | 10/1959 | Hallstron | 137/522 |
| 3,017,880 | 1/1962 | Brook | 128/351 X |
| 3,407,817 | 10/1968 | Galleher | 128/351 |
| 3,504,676 | 4/1970 | Lomholt | 128/351 |
| 3,529,596 | 9/1970 | Garner | 128/145.6 |
| 3,693,611 | 9/1972 | Ploss | 251/61.1 X |
| 3,707,151 | 12/1972 | Jackson | 128/349 B X |
| 3,731,691 | 5/1933 | Chen | 128/351 |
| 3,788,326 | 1/1974 | Jacobs | 128/349 B X |
| 3,938,551 | 2/1976 | Henkin | 137/522 X |

*Primary Examiner*—Edgar S. Burr
*Assistant Examiner*—Paul T. Sewell

[57] ABSTRACT

The connector member which connects a tracheal tube to the source of breathing air incorporates an auxiliary passage having an entrance device for inflating the cuff with the breathing air, the entrance device responding to raised pressure in the connector to admit the breathing air for filling the cuff and responding to decrease in the pressure to close the auxiliary passage at a desired level for retaining sealing pressure in the cuff.

16 Claims, 6 Drawing Figures

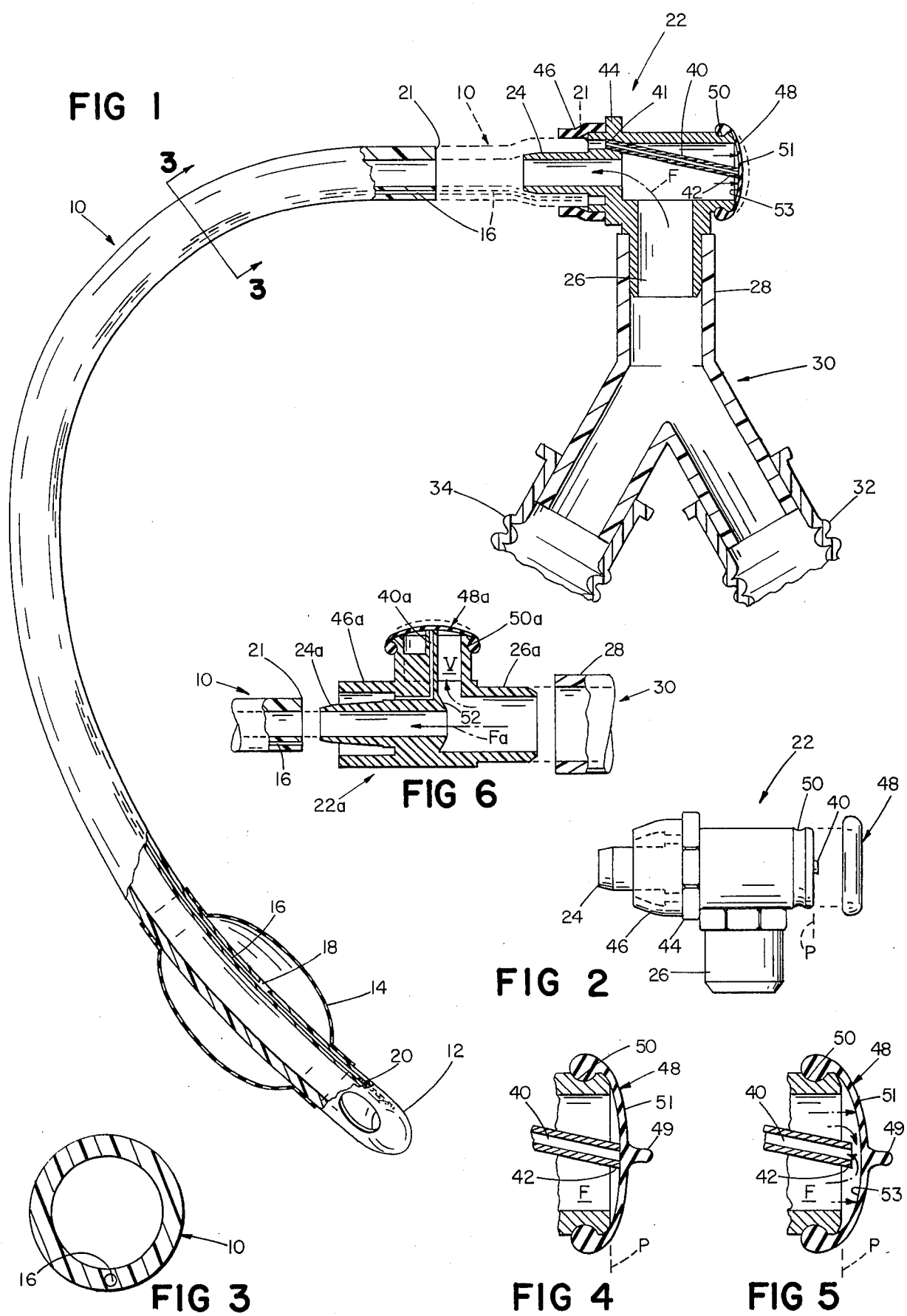

CUFF INFLATION FOR TRACHEAL TUBES

BACKGROUND OF THE INVENTION

This invention relates to the inflation of cuffs of endotracheal tubes, being addressed generally to the same problems as is my prior U.S. Pat. No. 3,565,079.

The inflated cuff of an endotracheal tube forms a seal with the trachea, serving, during the inspiration phase of the respiratory cycle, to maintain pressure in the lungs, and during all phases, serving to block aspiration of liquids or solids from the mouth into the lungs.

As is well known, it is desirable for the cuff inflation pressure to be of low value consistent with maintenance of a good seal. The lower the pressure, the lesser the danger of damage to the tracheal tissue due to blockage of blood flow, etc. Also, it is desirable to achieve this inflation on an automatic basis, without opportunity for error by personnel administering the tube.

My prior patent, mentioned above, sought to achieve the low inflation pressure automatically using the breathing air from the respirator as the source of pressure. But difficulties with constructions shown in that patent have been encountered, relating to loss of sealing pressure during expiration and to design constraints inherently present. Though such difficulties may be overcome, no commercial product has yet resulted.

For other suggestions dealing with cuff inflation see for instance U.S. Pat. Nos. 3,504,676; 3,529,596 and 3,731,691.

SUMMARY OF THE INVENTION

The present invention provides an improved means for employing the air of the respirator or breathing circuit for automatically inflating the cuff. According to the invention the connector member at the proximal end of the breathing tube, outside of the patient, is provided with an auxiliary passage having an entrance device exposed to the breathing air. This entrance device responds to raised pressure in the connector during inspiration to admit pressurized breathing air to the auxiliary passage and responds to decrease in pressure during expiration, to seal the auxiliary passage at a desired pressure level. The auxiliary passage is connected to the inflation passage of the cuff, both of these passages being sized adequately to transmit inflation air. By this invention the structure for admitting air automatically to the cuff, located outside of the patient, avoids design constraints that would be imposed if the operative elements were located on the tube in the patient. The invention also permits the various operative parts to be well engineered for sure operation and inexpensive fabrication.

In preferred embodiments the entrance device comprises an elastic member one portion of which is seated against the inlet opening of the auxiliary passage and a second portion of which is exposed to the pressure of air in the connector. Pressure above a given level on this second portion deflects the elastic member to admit breathing air through the opening to the auxiliary passage. When pressure returns below that level, the member elastically retracts and the opening is resealed. Preferably the elastic member comprises a flat membrane secured about its periphery to the connector member and engaged centrally upon the opening, the opposite side of the membrane being exposed to atmospheric pressure. Preferably also this membrane has a peripheral elastic flange tightly fitted in self-retaining relationship upon the connector member.

Also in preferred embodiments the inflation passage is integrally formed in the wall of the breathing tube, extending from the distally located cuff to the proximal butt end of the tube, and the auxiliary passage of the connector has an outlet connected to the proximal end of this inflation passage; an air scoop is disposed to intercept breathing air in the connector and direct the air pressure against the membrane; the connector has an inner nipple for insertion into the end of the breathing tube and an outer sleeve for sealing about the cylindrical exterior of the tube, these parts cooperating to form an airtight connection between the auxiliary and inflation passages; and the outer sleeve comprises an integral portion of the connector.

These and other objects and features will be understood from the following description of a preferred embodiment taken in conjunction with the drawings.

BRIEF DESCRIPTION OF THE DRAWINGS

FIG. 1 is a cross-sectional view of an endotracheal tube assembly according to the invention;

FIG. 2 is a side view of the connector of the assembly;

FIG. 3 is a cross-section of the breathing tube taken on lines 3—3 of FIG. 1;

FIGS. 4 and 5 are views on an enlarged scale of the membrane portion of the connector shown in FIG. 1, and FIG. 6 is a cross-section of another preferred embodiment.

DESCRIPTION OF THE PREFERRED EMBODIMENT

Referring to the figures, an elongated, curved breathing tube 10 of usual material, e.g., of polyvinylchloride, is formed at its distal end 12 for insertion into the patient's trachea. Near this end the tube carries an annular sealing cuff 14 which surrounds the breathing tube 10, the cuff arranged to engage the walls of the trachea. A filling passage 16 is integrally formed in the wall of the tube as shown in FIG. 3, being provided throughout the length of the tube during the extrusion process. Within the cuff 14 an opening 18 is formed in the wall to admit air from the filling passage 16 to the cuff while at the extreme distal end at 20 the unuseful extension of the filling passage is sealed. The filling passage extends to the proximal butt end 21 of the tube 10, shown in FIG. 1 in solid lines disconnected and in dotted lines connected to the connector 22. The filling passage 16 is amply sized, e.g. of 2 millimeter diameter, to enable adequate flow and pressure equilibration using the pressure of the breathing air for filling. The connector 22 comprises a nipple 24 arranged for insertion into the end of the breathing tube 10 in usual fashion, and a second nipple 26 arranged for insertion into the discharge end 28 of a Y-fitting 30 which is connected to the large bore hoses 32 and 34 of the breathing circuit. The connector 22 forms a connecting flow path F from the Y-fitting 30 to the breathing tube 10, thus introducing pressurized air to the trachea of the patient during inspiration and allowing return of that air when the pressure is lowered during expiration. An auxiliary passage 40 is provided within the connector member 22, shown here as formed by a straight portion of a hollow tube. The downstream end 41 of this tube passes through flange 44, and is exposed for communication with filling passage 16 in the wall of the breathing tube. A sealed connection between that auxiliary passage 40 and the filling passage 16 is provided by a sleeve member 46 which extends from the connector to tightly engage the cylindrical exterior of the tube 10. The inlet end 42 (FIGS. 4 and 5) of passage 40 is positioned to be exposed to the pressure of air in connecting flow path F. However it is sealed by diaphragm 48. Diaphragm 48, e.g. of rubber, is stretched over mounting rim 50 of the connector in self-retained position, and is distended, in the solid line position shown in FIGS. 1 and 4 to seal the end 42 of the auxiliary passage when there is no pressure at path F, tension being applied to the body of the membrane due to the projected position of end 42 relative to end plane P. The inside surface 53 of the diaphragm 48 is exposed to the pressure of air in flow path F while the outer surface 51 is exposed to ambient pressure. During operation, when the air pressure rises in flow path F, e.g., in the first cycle of operation, the pressure acting in the direction of arrows upon the inner surface of the diaphragm forces the diaphragm to the position shown in FIG. 5 and in dotted lines in FIG. 1, disengaging the end 42 of passage 40, allowing the entry of pressurized air through the auxiliary passage 40, thence along the filling passage 16 to the cuff 14. Then, when the pressure of the air in flow path F decreases during the cycle, the diaphragm elastically retracts from its dotted line to solid line position of FIG. 1, sealing the end 42 of auxiliary passage 40 before the pressure has completely diminished, this occurring at a level set by the design stress for the membrane. During the next cycle of the unit, again the diaphragm is distended and more air flows through the auxiliary passage 40 and filling passage 16 so that, in a few cycles the cuff is filled. Thereafter the cuff remains full, with internal pressure influenced by the respirator pressure during the inspiration phase and maintained, during the expiration phase, at a reduced desired level determined by the force exerted by the diaphragm upon the opening 42. The thus inflated cuff forms a seal with the tissue of the trachea which is maintained through both inspiration and expiration of the patient, providing the seal desired for control of the breathing function and preventing aspiration of substance past the endotracheal tube.

It will be noted that the preferred embodiment of the figures avoids the need for any separate lumen for filling of the cuff, and the endotracheal tube can have a smooth surface suitable for insertion into the trachea of the patient through the nasal passages.

When designed for production, the connector may be formed as a single injection molded unit, for instance the auxiliary passage being formed integrally in the body of the connector. In such a construction an annular space may be provided between the passage 16 and the auxiliary passage 40 to ensure connection regardless of the relative rotation of the parts.

As shown in FIGS. 4 and 5 preferably the membrane 48 is provided with a projection 49 exposed to be grasped by the person administering the tube, enabling the membrane to be manually operated to release cuff inflating pressure, as may be desired prior to removal of the tube from the patient.

In the embodiment of FIG. 6 the principles of construction are the same as in the embodiment of FIGS. 1-5 except that the inlet and outlet nipples 24a and 26a 26a axially aligned and the passage 40a leads to the side of the connector unit, where a membrane 48a is attached. The membrane is exposed to volume V which receives breathing air by the intercepting action of air scoop 52 projecting into the breathing air flow path Fa of the connector.

In usual use of either embodiment a seal is achieved by use of the manually actuated or automatic respirator after a few cycles. Should it be desired to expedite the inflation of the cuff it is possible to seal the tracheal tube so that full static pressure generated by the respirator is available to act upon the entrance device and auxiliary and filling passages. For this purpose the person administering the tube may squeeze it near the point of attachment to the connecting member in a manner to occlude the main air path but not the filling passage, or a valve member may be incorporated in the connector member for this purpose.

What is claimed is:

1. In a tracheal tube assembly comprising a breathing tube for insertion into the trachea, an inflatable cuff surrounding the tube to form a seal with the walls of the trachea, an inflation passage for admitting inflation air to the cuff, and a connector member in the connecting flow path for breathing air between a source of periodically pressurized breathing air and the proximal end of said breathing tube, the improvement wherein an auxiliary passage is incorporated in said connector member and has an entrance device exposed to the pressure of said breathing air in said connecting flow path, said entrance device incorporating a movable element responsive to raised pressure of said breathing air to move to a position to admit pressurized breathing air directly into said auxiliary passage, and responsive to decreased pressure to move to a position to seal said auxiliary passage from said breathing air, said auxiliary passage connected to said inflation passage, said passages cooperatively sized to transmit air at breathing pressure from said breathing air source during the inspiration phase to inflate said cuff.

2. The tracheal tube assembly of claim 1 wherein said movable element comprises an elastic member having a portion sealed against an opening into said auxiliary passage and an adjacent portion of said member exposed to air pressure in said connecting path whereby rise in said pressure elastically deflects said member from said opening, to admit said breathing air pressure directly to said auxiliary passage.

3. The tracheal assembly of claim 2 wherein said elastic member includes a projection exposed to be grasped, to enable manual release of pressure in said cuff.

4. The tracheal tube assembly of claim 1 wherein said movable element comprises a generally flat membrane held about its periphery to said connector member and engaged centrally upon an opening into said auxiliary passage, the opposite side of said membrane exposed to atmospheric pressure.

5. The tracheal tube assembly of claim 4 wherein said membrane has a peripheral elastic flange portion tightly fitted in self-retaining relation with a cooperatively formed portion of said connector member.

6. The tracheal tube assembly of claim 1 wherein said inflation passage is integrally formed in the wall of said breathing tube, extending from the cuff to the proximal butt end of said tube, and said auxiliary passage of said connector having an outlet connected to the proximal end of said inflation passage and wherein said connector has an inner nipple for insertion into the end of said breathing tube and an outer sleeve for sealing about the cylindrical exterior of said tube cooperating to form an airtight connection between the inlet to said inflation passage lying at the butt end surface of said breathing tube, and said auxiliary passage.

7. The tracheal tube assembly of claim 6 wherein said outer sleeve comprises an integral portion of said connector.

8. For use with a tracheal tube comprising a breathing tube for insertion into the trachea, an inflatable cuff surrounding the tube to form a seal with the walls of the trachea, and an inflation passage for admitting inflation air to the cuff, a connector member for defining part of the connecting flow path for breathing air between a source of periodically pressurized breathing air and the proximal end of said breathing tube, said connector member incorporating an auxiliary passage having an entrance device exposed to the pressure of said breathing air in said connecting flow path, said entrance device incorporating a movable element responsive to raised pressure to move to a position to admit pressurized breathing air directly into said auxiliary passage, and responsive to decreased pressure to move to a position to seal said auxiliary passage from said breathing air, said auxiliary passage adapted to be connected to said inflation passage to inflate said cuff with air from said breathing air source.

9. The tracheal tube connector of claim 9 wherein said movable element comprises an elastic member having a portion seated against an opening into said auxiliary passage, and an adjacent portion of said member exposed to air pressure in said connecting path whereby rise in said pressure elastically deflects said member from said opening, to admit said breathing air pressure directly to said auxiliary passage.

10. The tracheal tube connector of claim 9 wherein said elastic member includes a projection exposed to be grasped, to enable manual release of pressure in said cuff.

11. The tracheal tube connector of claim 8 wherein said elastic member comprises a generally flat membrane held about its periphery to said connector member and engaged centrally upon said opening, the opposite side of said membrane exposed to atmospheric pressure.

12. The tracheal tube connector of claim 11 wherein said membrane has a peripheral elastic flange portion tightly fitted in self-retaining relation with a cooperatively formed portion of said connector member.

13. The tracheal tube connector of claim 8 for use with a breathing tube in which said inflation passage is integrally formed in the wall of said breathing tube, extending from the cuff to the proximal butt end of said tube, said auxiliary passage of said connector having an outlet adapted to be connected to the proximal end of said inflation passage, said connector having an inner nipple for insertion into the end of said breathing tube and an outer sleeve for sealing about the cylindrical exterior of said tube, said nipple and sleeve cooperating to enable formation of an airtight connection between the inlet to said inflation passage lying at the butt end surface of said breathing tube, and said auxiliary passage.

14. The tracheal tube assembly of claim 13 wherein said outer sleeve comprises an integral portion of said connector.

15. The tracheal tube connector of claim 8 wherein said connector member includes an air scoop formation disposed in said flow path to divert breathing air to said entrance device.

16. The tracheal tube assembly of claim 1 wherein said connector member includes an air scoop formation disposed in said flow path to divert breathing air to said entrance device.

* * * * *

UNITED STATES PATENT AND TRADEMARK OFFICE
CERTIFICATE OF CORRECTION

PATENT NO. : 4,020,849
DATED : May 3, 1977
INVENTOR(S) : Richard R. Jackson

It is certified that error appears in the above-identified patent and that said Letters Patent are hereby corrected as shown below:

Under References Cited, "Hallstron" should be --Hallstrom--;

Under References Cited, "5/1933" should be --5/1973--;

Col. 3, line 66, delete "26a" and insert instead --are--.

Signed and Sealed this

Twenty-eighth Day of February 1978

[SEAL]

Attest:

RUTH C. MASON
*Attesting Officer*

LUTRELLE F. PARKER
*Acting Commissioner of Patents and Trademarks*